US00PP12766P2

(12) United States Plant Patent
Pinney, Jr.

(10) Patent No.: US PP12,766 P2
(45) Date of Patent: Jul. 9, 2002

(54) BIRCH TREE NAMED 'OENCI'

(75) Inventor: Thomas S. Pinney, Jr., Sturgeon Bay, WI (US)

(73) Assignee: Evergreen Nursery Company, Inc., Sturgeon Bay, WI (US)

( * ) Notice: Subject to any disclaimer, the term of this patent is extended or adjusted under 35 U.S.C. 154(b) by 0 days.

(21) Appl. No.: 09/395,055

(22) Filed: Sep. 13, 1999

(51) Int. Cl.[7] ..... A01H 5/00

(52) U.S. Cl. ..... Plt./216
(58) Field of Search ..... Plt./216

*Primary Examiner*—Bruce R. Campell
*Assistant Examiner*—Susan B. McCormick
(74) *Attorney, Agent, or Firm*—W. Dennis Drehkoff; Ladas & Parry

(57) ABSTRACT

A new and distinct cultivar of *Betula papyrifera* named 'Oenci' characterized by its broad, dense pyramidal growth habit, bark color changing from mahogany reddish brown to white at maturity, very high resistance to Bronze Birch Borer and drought resistance.

4 Drawing Sheets

The present invention comprises a new and distinct cultivar of a birch tree, botanically known as *Betula papyrifera*, and is hereto referred to by the cultivar name "Oenci".

BACKGROUND OF THE INVENTION

'Oenci' was discovered by the inventor in a group *Betula papyrifera* in test plots of Evergreen Nursery Company, Inc. in New Carlise, Ohio, in 1986. 'Oenci' was originated from the open pollinated cross in a birch selection/breeding program in Wooster, Ohio. The non-patented female parent was *Betula papyrifera*. The pollen parent was *Betula papyrifera*. 'Oenci' was first noticed with broad, dense pyramidal growth habit, white exfoliating bark and a very high resistance to the Bronze Birch Borer. The growth habit renders it ideal for clumping. The first act of asexual reproduction of 'Oenci' was accomplished by cuttings by the inventor from the initial selection in our test plot in New Carlisle, Ohio. Currently, asexual reproduction is accomplished by micropropagation or tissue culture in Olympia, Wash. Horticultural examination of selected units has demonstrated that the combination of characteristics as herein disclosed for 'Oenci' are firmly fixed and retained through its successive generations of asexual reproduction. 'Oenci' has been observed in Sturgeon Bay, Wis., and New Carlisle, Ohio, since 1986 and characteristics have been stably maintained. The cultivar reproduces true to type. The new cultivar has not been observed under all possible environmental conditions. The phenotype may vary somewhat with variations in environment such as temperature, day length and light intensity, without a change in the genotype of a cultivar. The following observations, measurements, and comparisons describe the plants grown in New Carlisle, Ohio, and Sturgeon Bay, Wis. under natural field conditions which approximate those generally used in commercial operations.

SUMMARY OF THE INVENTION

The following traits have been repeatedly observed and are determined to be basic characteristics of 'Oenci' which in combination distinguish this birch tree as a new and distinct cultivar:

1. Distinctive broad, dense pyramidal growth habit with branching angles about 33–35°.

2. Bark color changes as the tree matures; from mahogany reddish brown turning to white.

3. Exfoliating bark when mature.

4. Very high resistance to the Bronze Birch Borer.

5. Moderate growth rate.

6. Drought tolerant.

The novel cultivar 'Oenci' can be compared with the nonpatented *Batula papyrifera*. The foregoing characteristics are distinctive from the nonpatented variety because the nonpatented variety has a loose oval growth habit, a brown bark that turns white at maturity, variable resistance to Bronze Birch Borer and is not drought tolerant.

BRIEF DESCRIPTION OF THE DRAWINGS

The accompanying color photographs show typical characteristics of 'Oenci', with colors being as true as possible with illustration of this type.

DETAILED BOTANICAL DESCRIPTION

Figure 1:
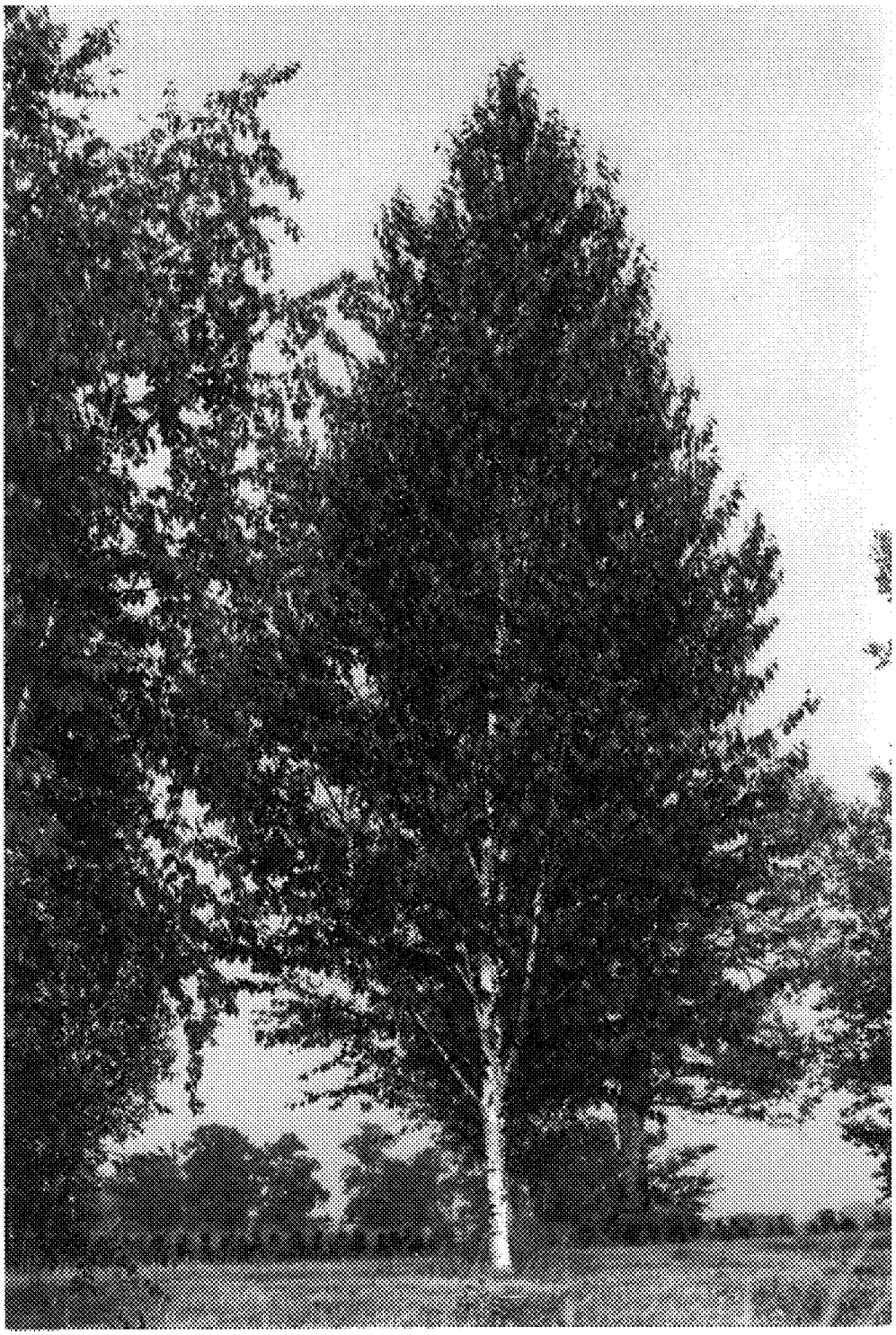
FIG. 1 is the side view of a specimen of 'Oenci' showing the pyramidal growth habit.
Figure 2:
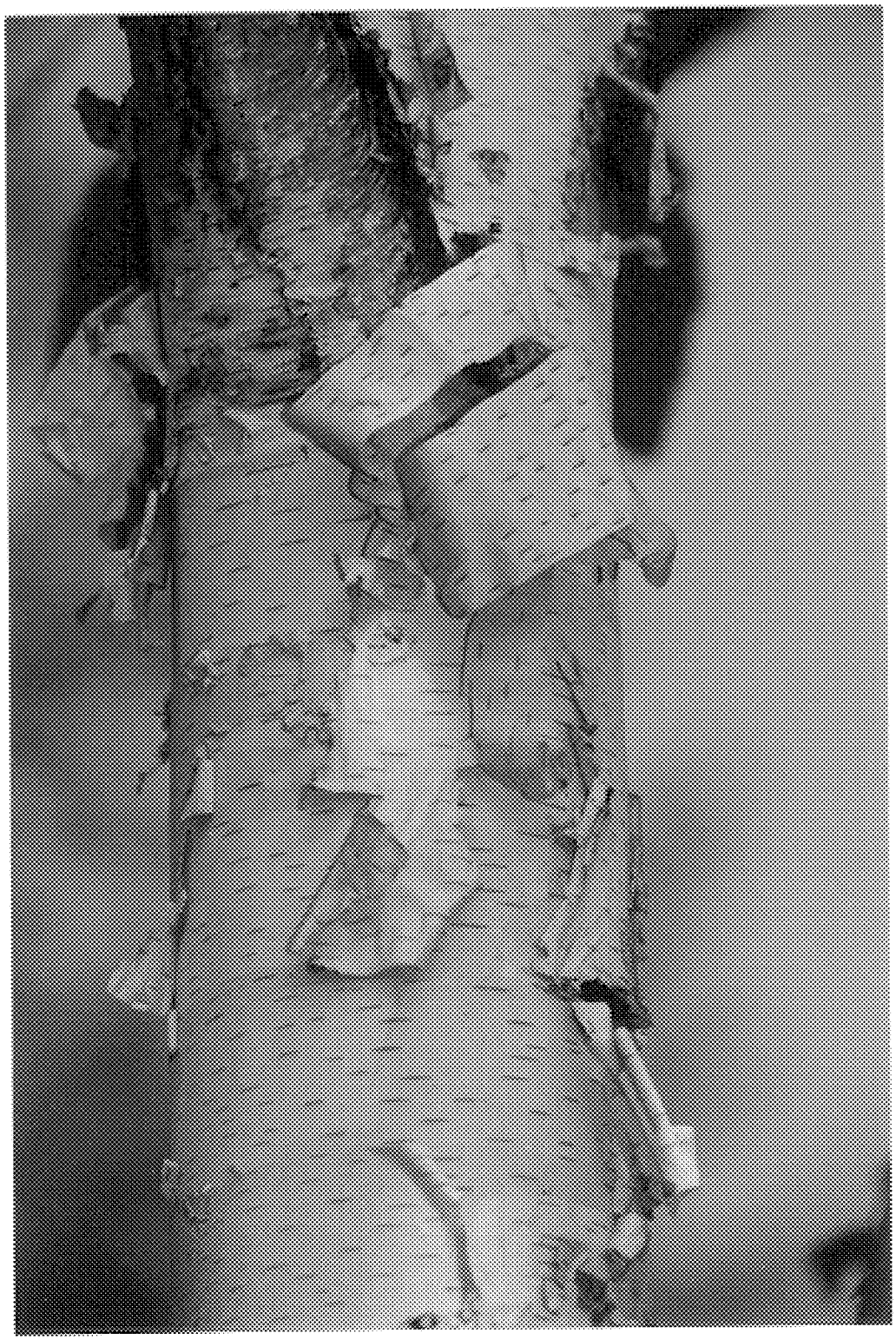
FIG. 2 shows the exfoliating bark.
Figure 3:
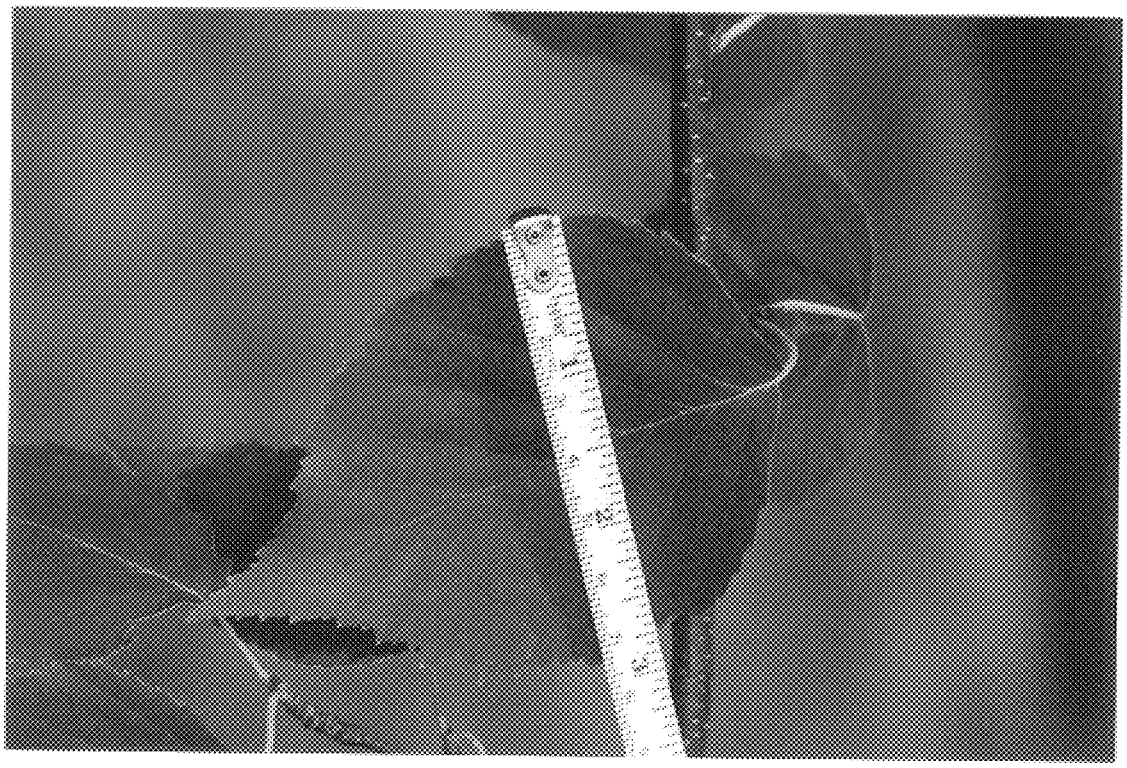
FIG. 3 shows a close-up of the upper side of a leaf.
Figure 4:
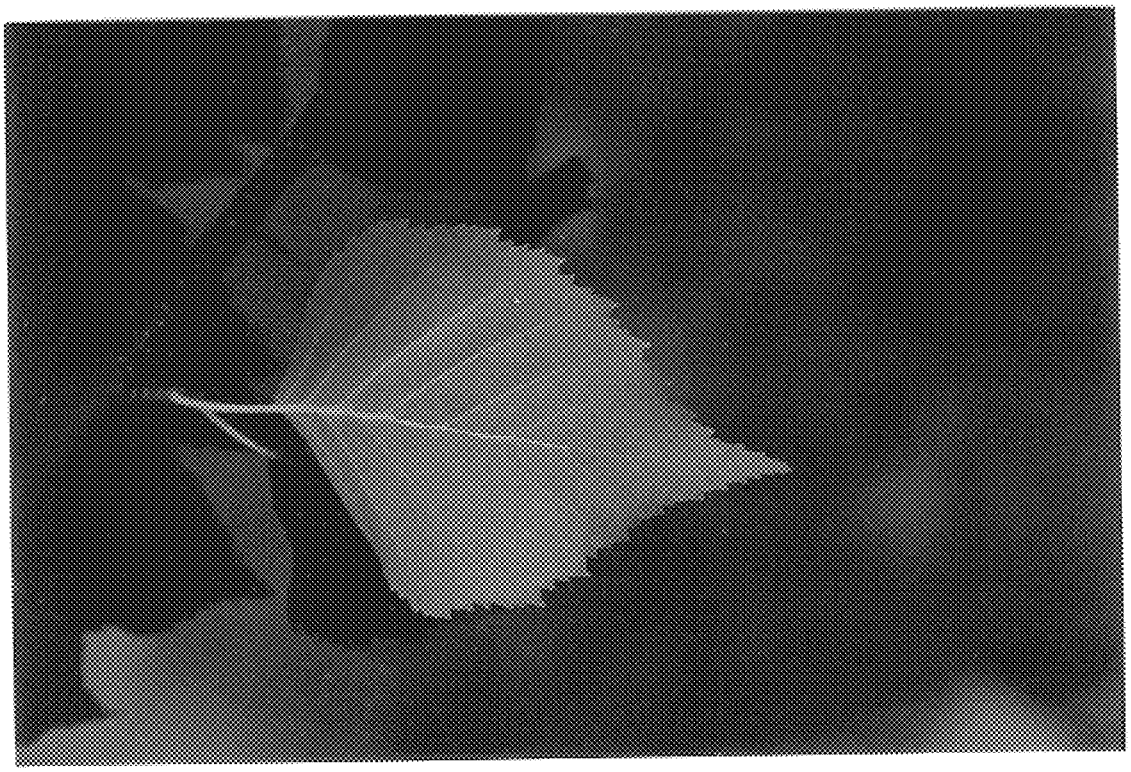
FIG. 4 shows a close-up of the under side of a leaf.
Figure 5:
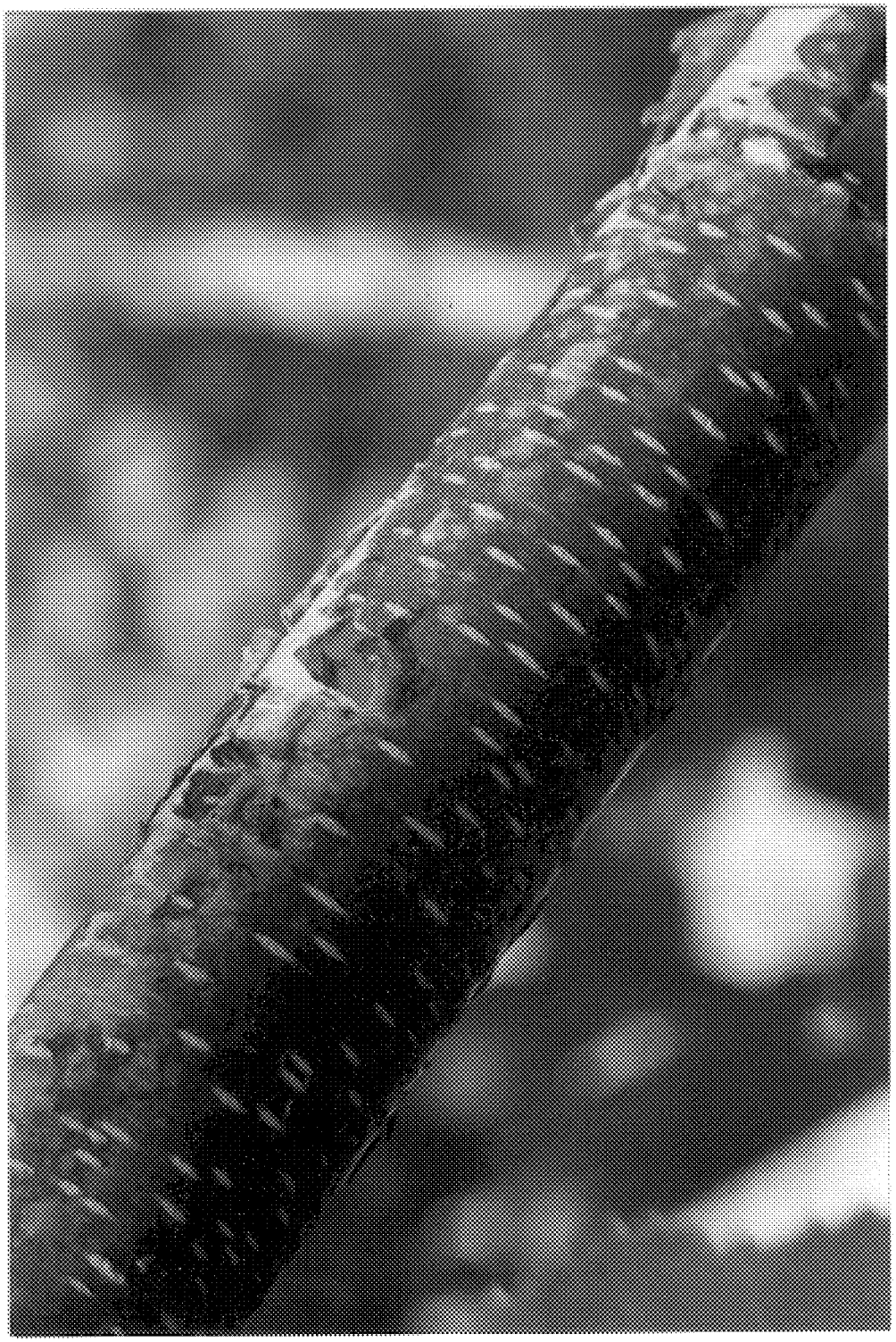
FIG. 5 shows a mahogany reddish stem as it changes to white.

In the following description, color references are made to The Royal Horticultural Society (R.H.S.) Colour Chart. The color values were determined in natural light in August 1999 in Sturgeon Bay, Wis.

Classification:

*Botanical.*—*Betula papyrifera* 'Oenci'.

Parentage:

*Origin.*—The plant was selected from a test plot of *Betula papyrifera* in New Carlisle, Ohio.

*Parentage.*—Seed parent: *Betula papyrifera*. Pollen parent: *Betula papyrifera*.

Tree:

*Trunk.*—Single-trunked tree. Size: Diameter at age 13 is approximately 12 cm four feet from the ground and the height is 8.5 m.

*Bark at maturity.*—White, fine textured, exfoliating close to (R.H.S. 155C) to greyed-orange bark (RHS 164D). Growth rate: moderate.

*Branches.*—Angle of attachment: 33–35°. Spacing: Between whorls 20–30 cm at a tree height of 2.4 m. Size when tree is 2.4 m and measured at 1.4 m: 3–4 cm. Bark: Color changes at about 4 years of age, from mahogany reddish brown (RHS 166A) turning to (RHS 155C) greyed-orange bark (RHS 164D) with exfoliation, fine texture. Lenticels: Small but numerous, size: 2–3 mm×1–2 mm. Color: greyed-orange (RHS 165D).

*Height.*—8.5 m at about 13 years of age.

*Growth habit or form.*—Broad, dense pyramidal, upright, when tree is 8.5 m high, it is about 4.5 m wide. Growth rate: moderate, about 0.6–1.5 m per year, depending on summer temperature, fertility and water availability.

*Foliage.*—Size of leaf: Length: with petiole 6–16 cm, without petiole 5–13 cm; Width: 4–8 cm; Leaf arrangement: alternate; Shape of leaf: rounded base, ovate to cordate with tip acuminate, acuminate apices and double serrate margins; Texture: Smooth; Ribs and veins: mid-rib with 16 veins (RHS 145B) alternate. Pubescence distribution: on under side mid rib and vein axils; Quantity: Singles or spurs of two or more, usually 2–3 leaves, common per spur, approximately 17 leaves/50 cm of stem. Color: upper side, green (RHS 137A), under side dark green (RHS 147B). Petiole: Length: 1–2.5 cm. Diameter: 0.5–2 mm; Color: (RHS 145C). No stipules.

*Disease and pest resistance.*—Very high resistance to Bronze Birch Borer as compared with about 240 other trees in New Carlisle, Ohio. Highly resistant to Leafhoppers.

*Disease and pest susceptibility.*—Moderately susceptible to leafminor.

*Winter hardiness/drought/heat resistance.*—Winter hardiness in Zone 3 and good drought/heat resistance in Zone 7.

*Flowers.*—None have been observed to date.

*Reproductive organs.*—Typical of the species.

*Comparison with other plants.*—Comparison of this cultivar with 'Renci' is as follows:

DIFFERENCES

| | 'Renci' | 'Oenci' |
|---|---|---|
| Shape | Pyramidal | Broad dense pyramid |
| Bark | White-essentially Non-effaliality | White - exfoliating |
| Branches Color | RHS 200A | RHS 166A |
| Leaf Color | RHS 147A | RHS 137A |
| Draught tolerance | Good | Excellent |

What is claimed is:

1. A new and distinct cultivar of birch tree named 'Oenci' as illustrated and described.

* * * * *